United States Patent [19]

Sei

[11] Patent Number: 5,213,981
[45] Date of Patent: May 25, 1993

[54] BEDDING APPARATUS

[75] Inventor: Masahiro Sei, Kanagawa, Japan

[73] Assignee: Kabushiki Kaisha Komatsu Seisakusho, Tokyo, Japan

[21] Appl. No.: 725,096

[22] Filed: Jul. 3, 1991

Related U.S. Application Data

[62] Division of Ser. No. 490,580, May 17, 1990, Pat. No. 5,049,505.

[30] Foreign Application Priority Data

Sep. 27, 1988 [WO] PCT Int'l Appl. ... PCT/JP88/00981

[51] Int. Cl.⁵ .................... C12M 1/34; C12M 3/00; A01C 1/00
[52] U.S. Cl. ...................... 435/284; 47/61; 47/62; 435/291; 435/311
[58] Field of Search ............... 47/62, 61, 85; 435/284, 435/311, 240.45, 240.46, 240.47, 291; 356/425, 402, 441, 39

[56] References Cited

U.S. PATENT DOCUMENTS

| | | | |
|---|---|---|---|
| 3,746,864 | 7/1973 | Tick et al. | 356/435 |
| 4,408,414 | 10/1983 | Lehle et al. | 47/58 X |
| 4,545,147 | 10/1985 | Janick et al. | 47/58 |
| 4,660,971 | 4/1987 | Sage et al. | 356/39 |
| 4,752,447 | 6/1988 | Kimmel et al. | 356/402 |
| 4,839,292 | 6/1989 | Cremonese | 435/311 |
| 4,855,236 | 8/1989 | Levin | 435/311 |

Primary Examiner—Jill A. Johnston
Attorney, Agent, or Firm—Diller, Ramik & Wight

[57] ABSTRACT

A bedding apparatus includes a culture mechanism for accommodating a cultured tissue together with a nutrient solution for culturing the tissue; a selecting mechanism selects cultured tissues on the basis of color and magnitude, and the selected culture tissues are bedded one-by-one on a nutrient medium. A density detecting mechanism detects the density of the cultured tissues and responsive thereto a feeding mechanism selective feeds nutrient solution or pure water to the cultured tissues.

6 Claims, 20 Drawing Sheets

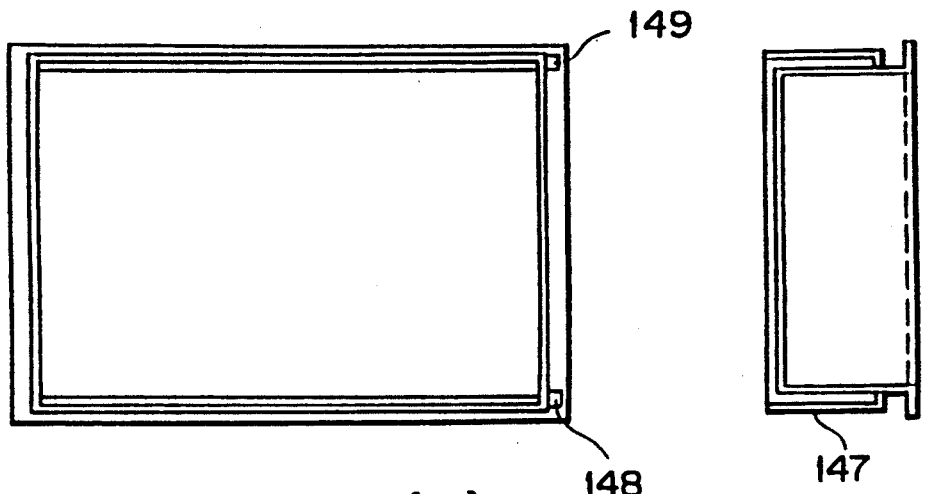
FIG.13(a)
FIG.13(b)
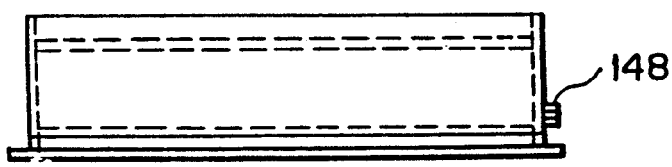
FIG.13(c)

BEDDING APPARATUS

This application is a division, of application Ser. No. 07/490,580, filed May 17, 1990 now U.S. Pat. No. 5,049,505.

TECHNICAL FIELD

The present invention relates to bedding and breeding apparatus, and more particularly to apparatus which select cellular bodies and bed them on a nutrient-solution nutrient medium, and ambient control apparatus which consistently culture and acclimate tissue-cultured seedlings within a culturing chamber.

BACKGROUND ART

Recently, a research on a plant biotechnology which breeds useful plants by taking out various cells and tissue organs which constitute individual plants, and performing various artificial operations such as cell fusion, mutagen processing, gene manipulation, etc., and reproducing individual plants has drawn attention.

For example, a method of breeding seedlings by using shoot apex culture, whose basic concept is shown in FIG. 26, includes a stage of bedding and multiplying on an agar culture medium within a container plant tissues cut from a predetermined portion of a plant, a germinating stage of transplanting the multiplied plant tissues into another container and causing them to germinate therein, a root-making stage of dividing, cutting and transporting causing the germinated plant portions into another container and causing to make root, and an acclimating stage of taking the plant portions which have made out of the container, washing them in an agar, humidifying them in a light-screened state within an acclimating device to cause the washed plant portions to make root again and to acclimate them to the ambience. After acclimation, they are transplanted into a pot for breeding purposes. In the respective multiplying, germinating and root-making stages, they are cultured using the agar culture medium which contains the respective optimal ingredients, and transplantation is required to be made at least once in each of the culturing stages, which requires significant labor and cost problematically.

It is desirable to exchange culture medium components and to feed gas in each stage in order to optimize the gas and the culture medium components at all times. However, gas is difficult to feed and discharge gas within a test tube. Transplantation is necessarily required to exchange the culture medium components in the agar culture medium, so that the components conditions are selected substantially once at most at each of the stages in view of working efficiency and damage to living plants. Therefore, especially, there are many cases in which roots made at the root-making stage insufficiently extends due to failure of oxygen to thereby become malformed.

When young plants which have made root are moved to the acclimating stage, they are moved to a planting nutrient medium such as vermiculite. At this time, washing is required to prevent the contamination with mold and bacteria because the agar culture medium used at the root-making stage contains sugar. This washing requires significant labor, can easily damage the roots and retard the growth of the young plants.

The inventors proposed a device which implants cultured tissues such as adventive buds or adventive embryos into a nutrient medium support impregnated with a nutrient medium solution disposed within a hermetically sealed container, feeds and discharges a nutrient medium solution to and from the nutrient medium support, and feeds and discharges the gas component to and from the container to optimize at all times the nutrient solution and gas necessary for culturing them to thereby cause the cultured tissues to make root and to acclimate to the ambient conditions (Specifications of Japanese Patent Applications Nos. 61-187691 and 61-187692).

According to this device, no transplantation is required and the gas and nutrient medium components are maintained in an optimal state, so that cultured tissues are grown well with high working efficiency. Also, in acclimation no transplantation is required and the cultured tissues are acclimated under good conditions without stopping the growth of the roots. Therefore, inexpensive and high-speed growth results—excellent effects.

However, tissue culture is very likely to be damaged by entering mold or bacteria. Therefore, handling must be performed on a clean bench. In addition, a skillful operator is required. It is difficult to adjust the nutrient medium solution, to feed and discharge gas many times while preventing the invasion of mold or bacteria, which is one cause to prevent the practical use of the tissue culture.

In order to multiply individual plants by tissue culture, shoot apexes and axillary buds are used from a standpoint of virus free.

Conventionally, one of the tissue culture methods using shoot apexes and axillary buds includes changing plant tissues, cut from the shoot apexes or axillary buds, to calluses in an agar culture medium containing plant growth regulator, for example, 2.4-D, etc., multiplying the calluses in the liquid nutrient medium, and passing the multiplied calluses through a sieve including a first filter of a 100 $\mu$m-screen and a second filter of a 50 $\mu$m-screen.

Thereafter, small cellar masses of a uniform size (50 $\mu$m $< X <$ 100 $\mu$m) remaining on the second filter are washed away in a liquid nutrient medium which contains 2.4-D free medium and then washed better and changed to adventive embryos in a new nutrient medium.

The resulting products are then filtered to obtain uniform-sized adventive embryos.

Thereafter, they are classified according to shape and color and bedded to the nutrient medium.

Such a work is done almost manually. In order to avoid contamination by various germs the work must be done on a clean bench, which requires careful and skilled techniques.

Especially in bedding, many adventive embryos cultured, for example in a tank, are planted manually one by one, so that the bedding process is a factor of hindering batch processing in the course of the entire operation.

In view of the above situation, the present invention has been made. It is an object of the present invention to provide a young plant breeding apparatus which prevents mold or bacteria from entering the apparatus and breeds the young plants inexpensively at high speeds.

In view of the above situation, the present invention has been made. It is an object of the present invention to facilitate the selection and bedding of cultured tissues, to sterilize cultured tissues and to improve the efficiency of the tissue culture.

DISCLOSURE OF THE INVENTION

In the present invention, a hermetically sealable culture box is provided which includes a nutrient medium support excellent in water holdability and hydrophilicity. A removable sterilizable germ entrance-preventive joint is connected at one end to the culture box. A gas feeding system and a plurality of nutrient medium solution feeding systems are provided. In accordance with the degree of growth of the cultured tissues, the joint is connected at the other end to the gas feeding system and to one of the nutrient medium solution feeding systems to thereby feed and discharge gas and a nutrient medium solution to and from the culture box.

According to such arrangement, the culture box is removably connected to the germ entrance-preventive joint, so that sterilization of the culture box is easy and the joint is also sterilized. Therefore, cultured tissues such as adventive buds or embryos are bedded to the nutrient medium support and appropriate culture solution components and gas are fed and discharged in a sterilized state sequentially with working efficiency in accordance with the degree of growth of the cultured tissues.

Transplantation is unnecessary in the movement from the root-making stage to the acclimating stage. The culture solution support with young plants which have made root is washed, the nutrient component containing sugar used for root making is eliminated, and appropriate nutrient solution components are continuously fed to the young plants, so that no roots are damaged.

Therefore, the young plants do not fade, well absorb from their roots the water content and nutrient solution component fed and continue to grow without being invaded by mold or bacteria.

The young plants continue to grow well without fading due to a change of stage and stoppage of growth, so that humidity can be reduced and light strength can be intensified for acclimation to thereby result in inexpensive and high speed breeding with high working efficiency.

The inventive young plants bedding apparatus includes culture means for accommodating cultured tissues together with a culture solution, selecting means including density adjusting means for feeding a constant quantity of a constant density solution containing a cultured tissue fed from the culture means and selecting the cultured tissues, and bedding means for dropping and bedding the selected cultured tissues from an end of a transfer pipe onto the nutrient medium at predetermined time intervals.

According to the apparatus, the selecting means selects the cultured tissues, so that bedding cultured tissues which have variation, etc., is prevented. Further, the cultured tissues are very easily selected and bedded under sterile conditions.

By density adjustment, the intervals at which the cultured tissues appear in the transfer pipe are adjusted. If the culture tissues are bedded at those intervals, they can be bedded very easily one by one.

BRIEF DESCRIPTION OF THE DRAWINGS

FIGS. 2(a)-(c) illustrate a culture box of the apparatus;

FIGS. 12(a)-(c) and

FIGS. 13(a)-(c) show modifications of a cooling structure of a culturing device;

BEST MODE CARRYING OUT THE INVENTION

Embodiment of the present invention will be described hereinafter in detail with reference to the drawings.

Figure 1:
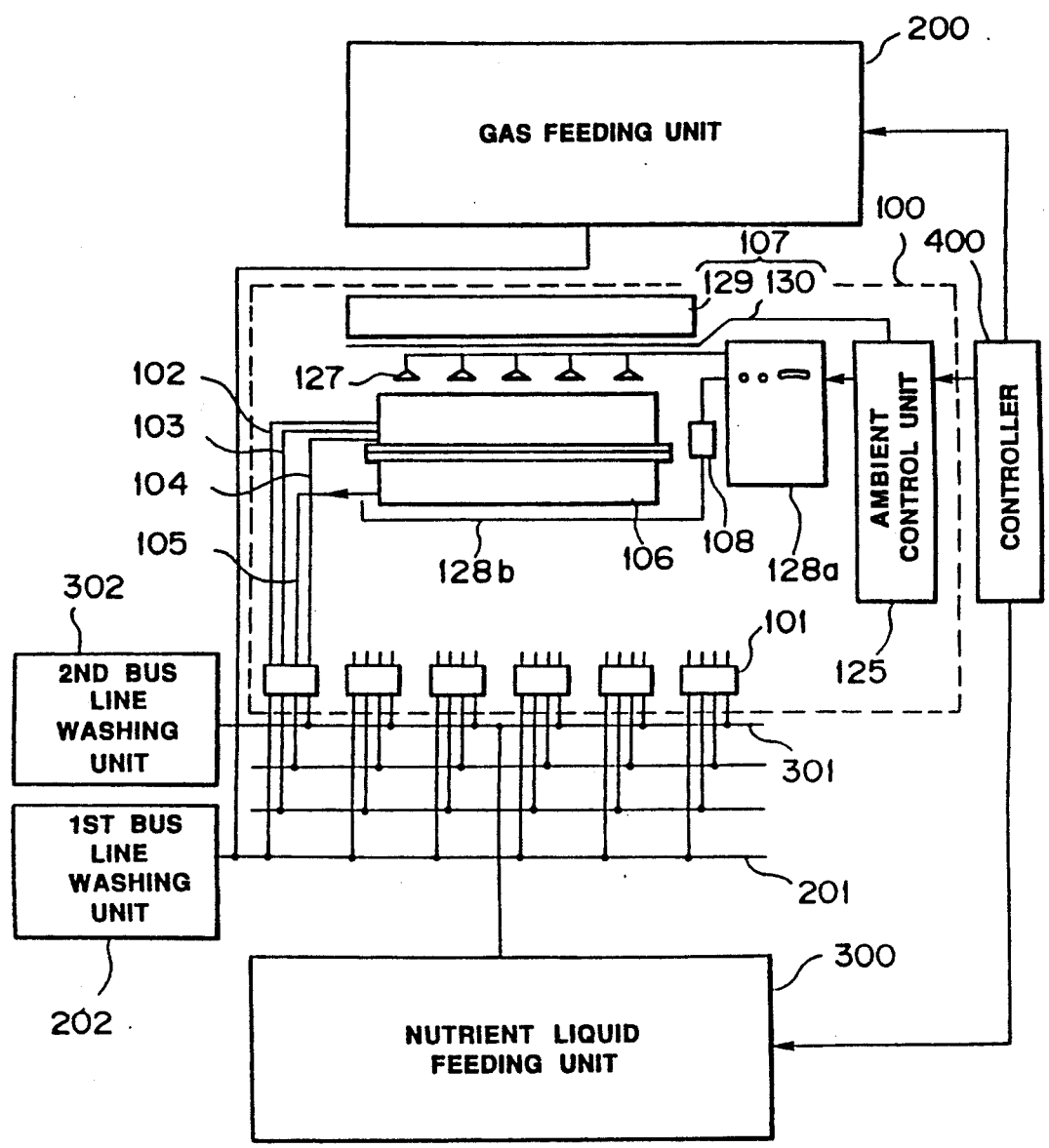
FIG. 1 illustrates a young plant breeding apparatus as an embodiment of the present invention.
Figure 17:
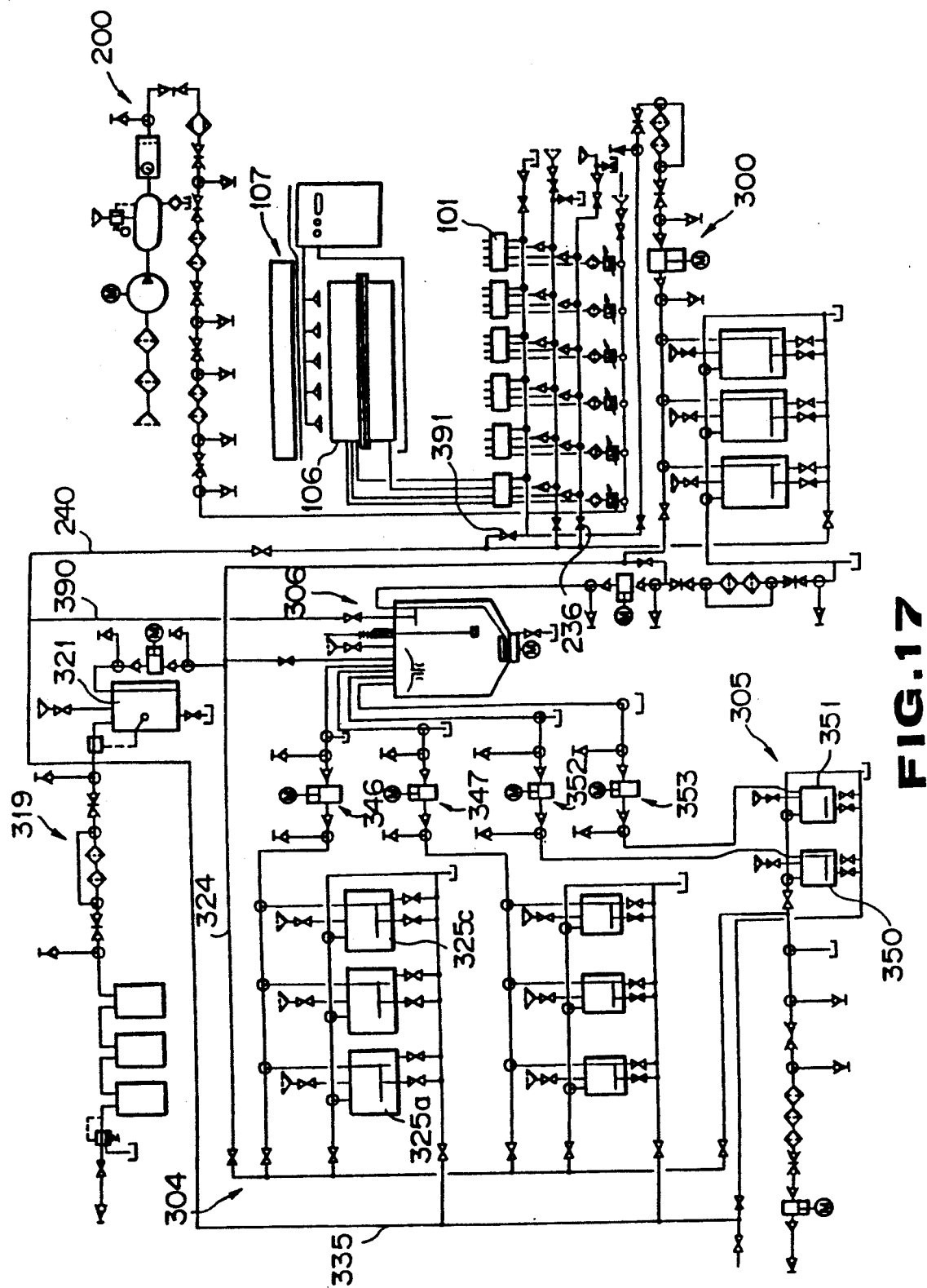
FIG. 17 illustrates the entire breeding apparatus as an embodiment of the present invention.

FIG. 1 schematically illustrates a young plant breeding apparatus as an embodiment of the present invention. (FIG. 17 illustrates the entire breeding apparatus.)

The breeding apparatus beds adventive embryos or buds grown by tissue culture and controls the feeding and discharging of a nutrient solution and a gas consistently from the root-making stage to the acclimating stage without transplantation. As shown in FIG. 1, it includes six culture units 100 (the remaining five culture units 100 are not shown) each including a culture box 106 which, in turn, includes a gas feeding pipe 102, a gas discharge pipe 103, a nutrient solution feeding pipe 104, and a nutrient solution discharge pipe 105, those pipes having a common removable germ-preventive joint 101 at one end; an illumination unit 107 which supplies desired light to the culture box; a temperature control unit 108 which controls the temperature of the culture box; a gas feeding unit 200 and a nutrient liquid feeding unit 300 which have a first and a second common bus line 201 and 301 removably connected through germ entrance-preventive joints 101 to the corresponding culture units 100; a control unit 400; a first and a second bus line washing unit 202 and 302 which wash the first and second bus lines, respectively. Thus, cultured tissues are bedded in the culture box 106. Quantities of the gas and nutrient solution corresponding to the degree of growth of the cultured tissues are fed from the gas feeding unit and the nutrient solution feeding unit through the common bus lines 201 and 301, respectively, to the respective culture units without transportation from the root-making stage to the acclimating stage. When the nutrient solution or the gas is changed, the bus lines are washed by the first and second bus line washing units to maintain a sterile state and breeding and acclimation are performed at high speeds.

FIGS. 2(a), (b) and (c) show a side view, a top plan view and an A—A line cross-sectional view, respectively, of each culture box 106. As shown, each culture box 106 includes a box body 106a and a lid 106b which hermetically seals the box body. The box body interior is covered with a water collecting material and a root entanglement-preventive sheet 111 superposed on the water-collecting material to prevent entanglement of the roots of the cultured tissues. Nutrient solution supports 113 of polyester wool or vermiculite are provided in the cellular spaces formed by partitions 112. A nutriment solution discharge pipe 105 extends through a flange 114 from the bottom of box body 106a. An exhaust liquid is discharged via capillary 115 accommodated in the flange so as to contact water collecting material 110. Gas feeding pipe 102, nutrient solution feeding pipe 104 and gas discharge tube 103 extend from the side of the box.

Gas feeding pipe 102 extends close to an end of a suction pipe 102a within the box body to draft and atomize the nutrient solution or water remaining in liquid reservoir 117 enclosed by frame 116 and fed from a nutriment solution feeding pipe 104 to thereby feed the atomized liquid to the cultured tissues on nutrient medium support 113. Frame 116 includes fixed plate 116a and adjusted plate 116b which cooperates with internal magnet 118a. Moving external magnet 118a from outside the height of adjusted plate 116b is adjusted. The quantity of atomization is adjusted in accordance with the level of water within the frame and a quantity of jetted gas and also the quantity of liquid is easily controlled. If adjusted plate 116b is raised to cause the mist to hit the adjusted plate, large liquid particles return to the liquid reservoir 117 to be atomized again, and only finer particles fill the culture box 106.

The direction of the nozzle of gas feeding pipe 102 may be altered when required.

Gas discharge pipe 103 has a funneled suction inlet (not shown) at an inner end to cause mist to sink and to be eliminated.

Figure 3:
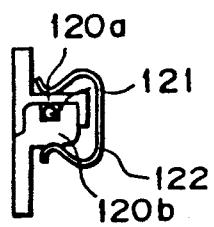
FIG. 3 illustrates a sealed structure of the culture box.

As shown in FIG. 3, box body 106a and lid 106b are joined by engaging a body flange and a lid flange 120a and 102b, provided around the peripheries thereof, through an O-like ring 121 and fastening them with clip 122 to thereby provide a hermetically sealed structure. The lid flange takes the form of a U in cross section to receive the body flange therein. The outer and inner branches of the U prevent from external and internal droplets, respectively, from reaching O-like ring 121.

Figure 2C:
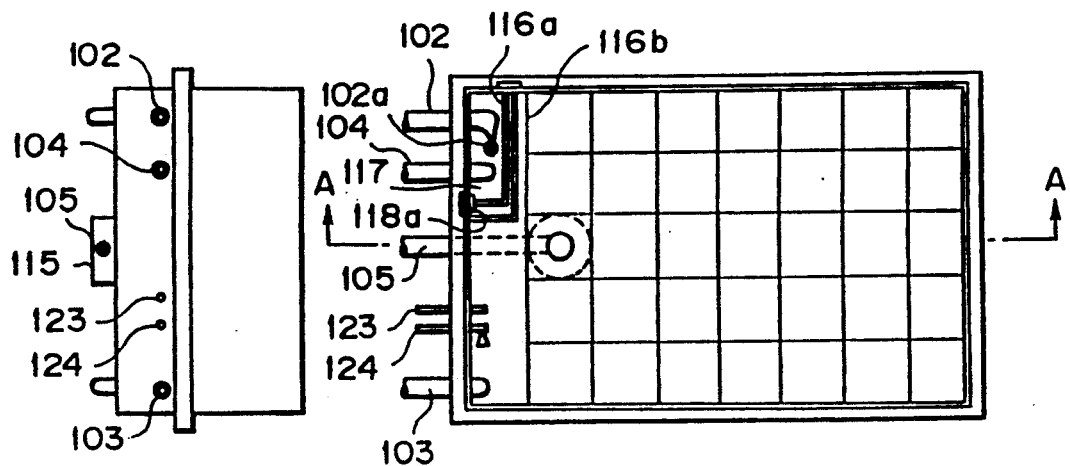
Figure 2C:
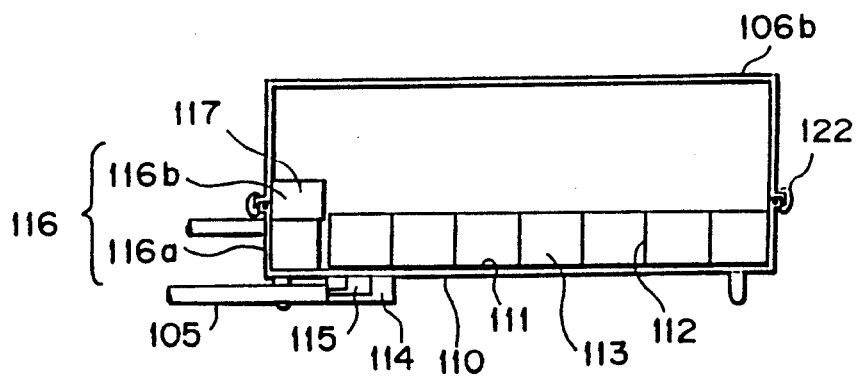

As shown in FIG. 2(c), capillary 115 disposed in flange 114 at the bottom of culture box 106, and the water collecting body are composed of porous ceramics, cotton, paper, etc., to collect the nutrient liquid content in the nutrient solution support 113 via a root entanglement-preventive sheet 111 and water collecting body 110. If the capillary holding force is high, the bubbling point is high to prevent passage of air and allow passage of only water, so that the nutrient solution content is discharged satisfactorily by slightly increasing the inner pressure of culture box 106 or suctioning nutrient solution discharge pipe 105.

Disposed on the side of the culture box are temperature sensor 123 and humidity sensor 124 the outputs of which are sent to ambient control unit 125 which processes the outputs for use as control data for light intensity, gas feeding, etc. The entire ambient control unit 125 is controlled by controller 400.

The culture box is irradiated with light and the upper portion of the box is transparent to light, so that the temperature of the box is raised. Thus, temperature control is performed by temperature control unit 108. As shown in FIG. 1, temperature control unit 108 which is operated in accordance with a command from ambient control unit 125 includes cooling water making unit 128a, cooling water nozzles 127 disposed above the culture box and cooling water receiver 128b disposed below the box. Cooling water from cooling water nozzles 127 is caused to overflow into receiver 128b to thereby cool the periphery of the culture box and control the internal temperature of the box.

Illuminating unit 107 includes a light source 129 of a metal halide lamp and an adjusting filter 130 which is controlled by ambient control unit 125 to thereby control the intensity and wavelength distribution of light illuminating culture box 106 in accordance with growth stage.

Figure 4A:
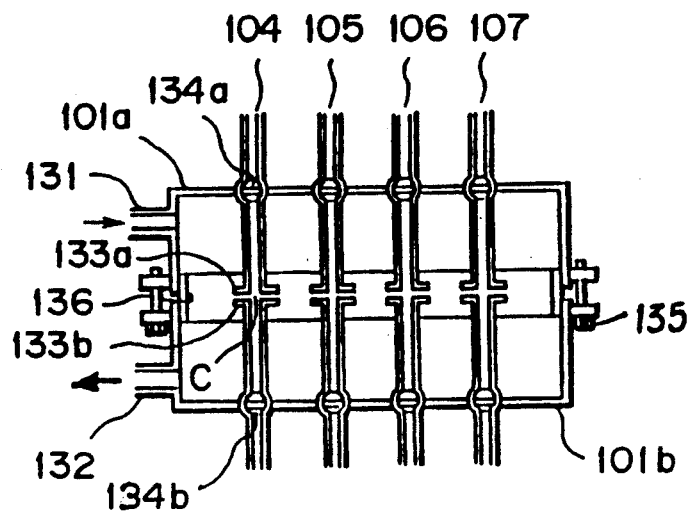
FIGS. 4(a) and (b) illustrate a germ entrance-preventive joint of the apparatus.

As shown in FIGS. 4(a) and (b), germ entrance-preventive joint 101 includes joint body 101a and lid 101b with steam feeding port 131 and steam discharging port 132, respectively. Joint body 101a and lid 101b have flanges 133a and 133b, respectively, at their ends, and have gas feeding pipe 102 and gas discharging pipe 103, nutrient solution feeding pipe 104 and nutrient solution discharging pipe 105 extending therethrough. As shown in FIGS. 2(a)-(c), in coupling, first, the culture box side (joint body side) with the nutrient solution support being mounted thereon is sterilized in autoclave. Adventive embryos are bedded in a clean bench using the bedding unit (not shown) or the like. With the valves 134a, 134b in the corresponding pipes being closed, the joint body is aligned and engaged with the joint lid through screw valves 135 with a gap between both the flanges under which condition high pressure steam of 2 kg/cm$^2$ at 121° C. is fed for ten hours from steam feeding port 131 to steam discharging port 132. In this way, the pipes extending from flanges 133a, 133b to valves 134a, 134b are sterilized.

Figure 4B:
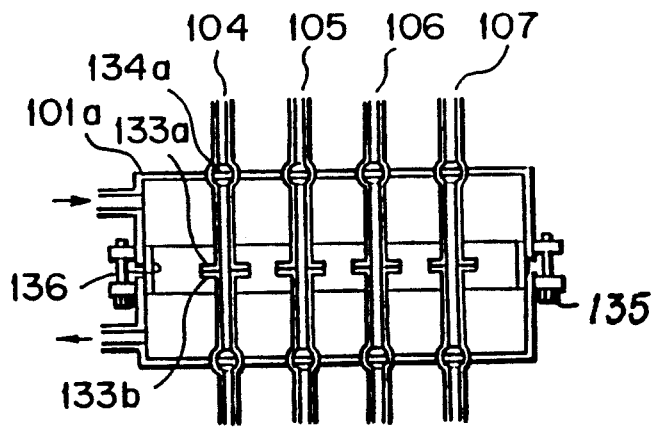

Thereafter, screw valve 135 is turned to slide on slider 136 to cause the joint body and the lid to contact each other to thereby cause flanges 133a and 133b to contact closely as shown in FIG. 4(b). Thus, when valves 134a and 134b are opened, connection under sterile conditions is achieved.

Gas feeding unit 200 will be described hereinafter.

Figure 5:
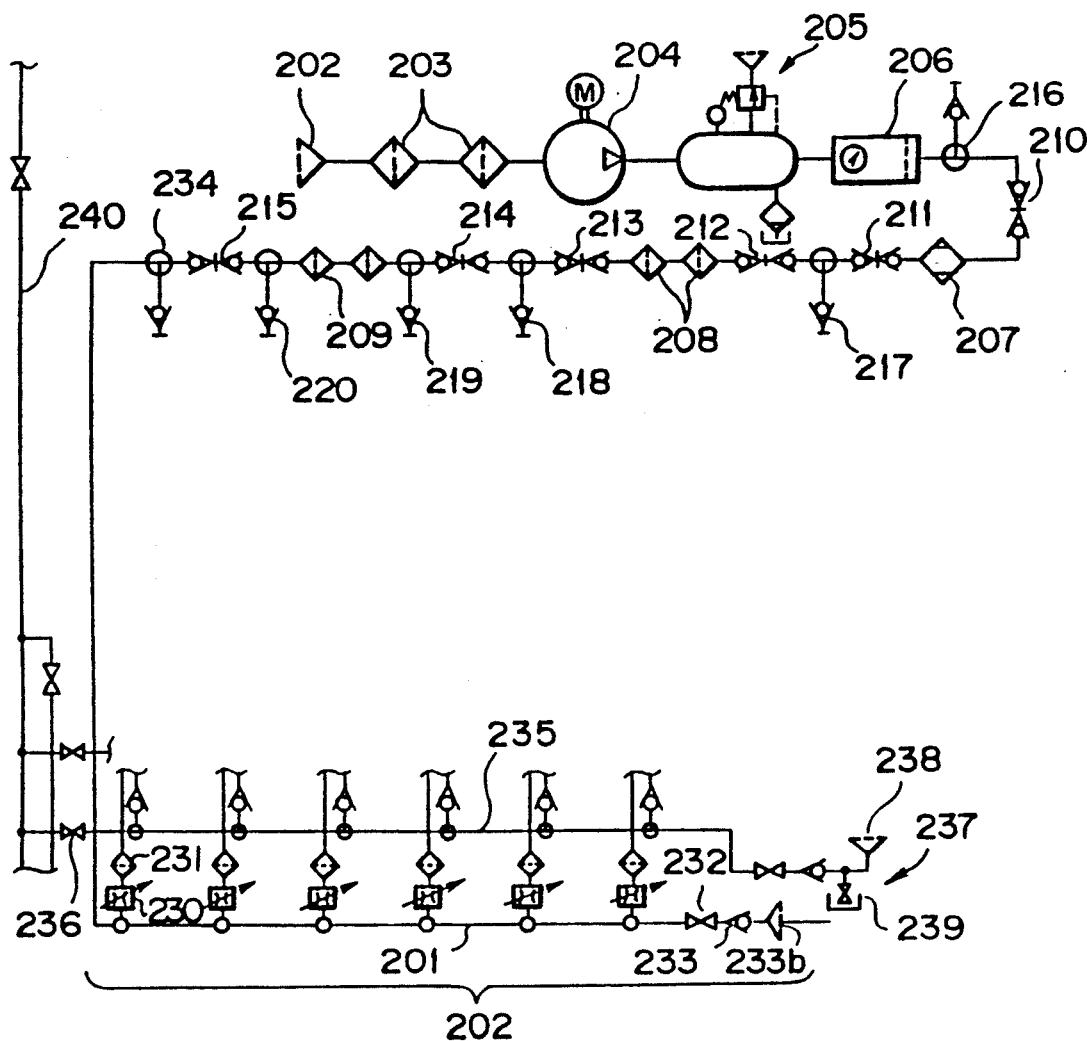
FIG. 5 illustrates a gas feeding system.

As shown in FIG. 5, gas feeding unit 200 includes a prefilter 202, first filter 203, pump 204, reseveroir tank 205 which stores air supplied by pump 204, pressure regulator 206, dryer 207, second filter 208, third filter 209 arranged in this order, and first bus line 201 which is connected to those elements sequentially to feed gas to the respective culture units 100. Dryer 207, second filter 208, third filter 209 can be switched, respectively, by check-valved joints 210, 211, 212, 213, 214 and 215. Check-valved three-way joints 216, 217, 218, 219 and 220 are distributed along the line for sterilization in exchange. For example, when second filters 208 are replaced with new ones, dry high pressure air is fed from check-valved three-way joint 217 and discharged from check-valved joint 218 to thereby sterilize joints 212 and 213. At this time, a heater (not shown) may be provided around each of second and third filters 208 and 209 to thermally sterilize them. These filters may be provided in parallel such that one of them is replaced and sterilized without stopping gas feeding.

Prefilter 202 and first filter 203 may be performed by using a heater disposed around each of them when required.

Figure 6:
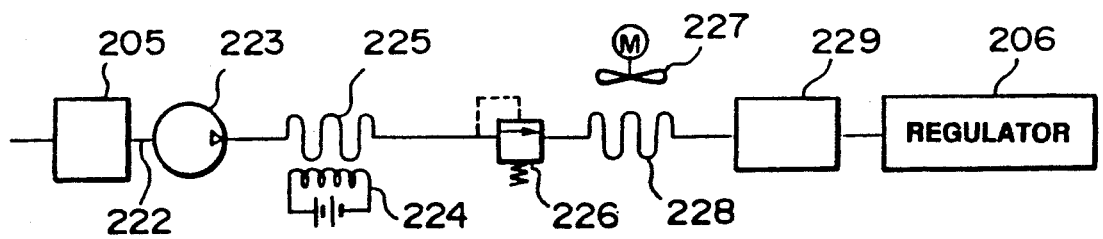
FIG. 6 illustrates an air sterilizing device.

As shown in FIG. 6, air sterilizing unit 221 may be provided between tank 205 and regulator 206 to thereby perform pressure sterilization (at 121° C. for 10 minutes). Air sterilizing unit 221 includes pump 223 which pumps out air through suction pipe 222 from reservoir tank 205, heater pipe 225 wound by a heater 224, relief valve 226, cooling pipe 228 with fan 227, and sterilizing tank 229 which is connected to regulator 206.

The gas (air herein) fed from the gas feeding unit passes from the first bus line through throttle valve 230, filter 231, and germ entrance-preventive joint 101 of each culture unit, and gas feeding pipe 102 to culture box 106. A quantity of gas fed is regulated by regulator 206. Instead of throttle valve 230 an orifice may be used.

The first bus line is connected at one end through valve 232 to check-valved joint 233 and bleeder 233B. Thus, dry high-pressure air is fed from three-way joint 234 on the other end (gas feeding side) of the first bus line toward joint 233 to perform sterilization and purification. This arrangement constitutes first washing unit 202.

The gas discharged from the culture box through gas discharge pipe 103 is discharged through gas discharge line 235 to gas discharge unit 237. Gas discharge line 235 is connected to first washing water feeding line 240 through valve 236 so as to feed washing water to gas discharge unit 237 therethrough for cleaning purposes. Reference numeral 238 denotes a bleeder; and 239, a drain.

Figure 7:
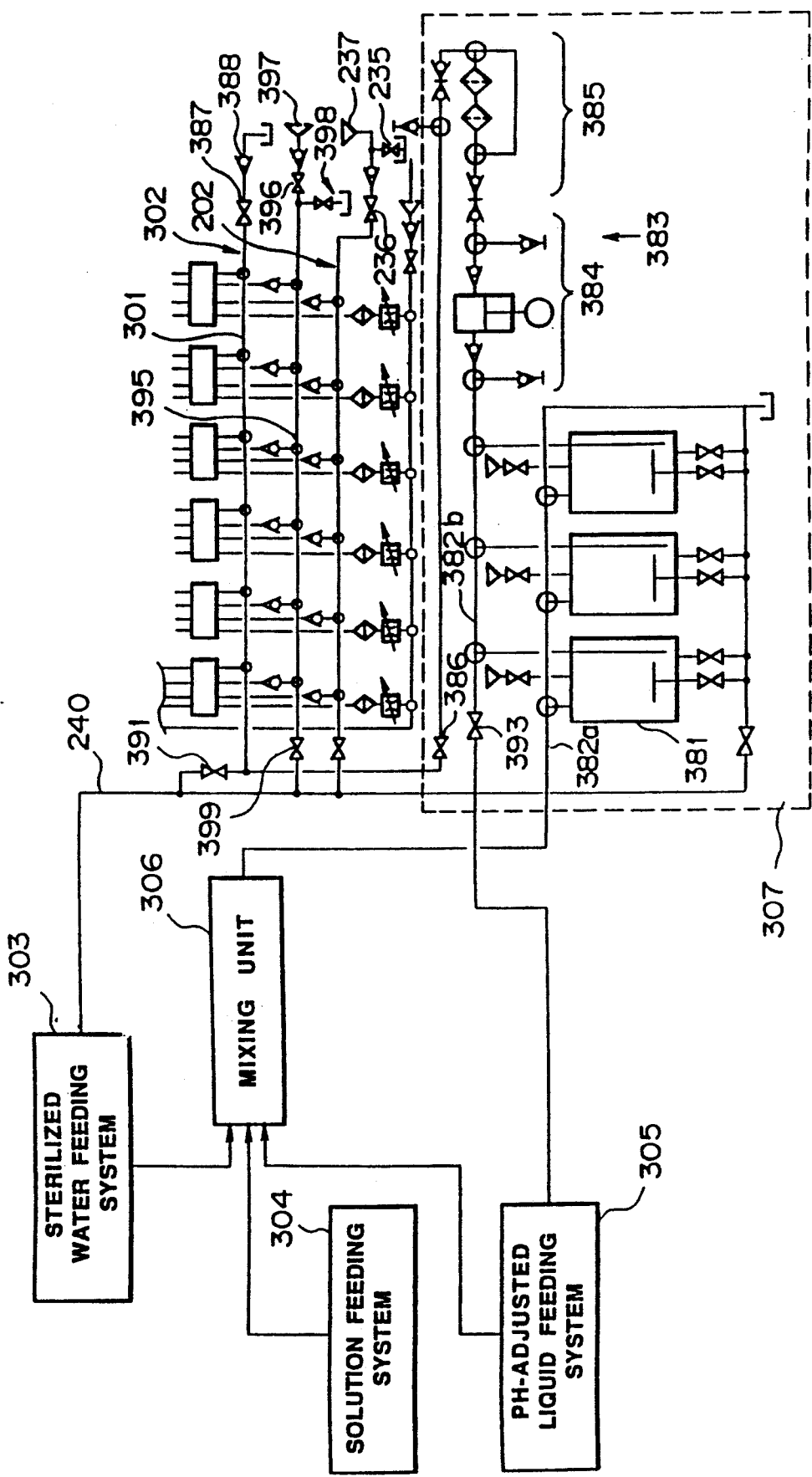
FIG. 7 illustrates a nutrient liquid feeding system.

Nutrient solution feeding unit 300 will now be described. As shown in FIG. 7, nutrient solution feeding unit 300 includes sterilized reducing water feeding system 303, solution feeding system 304 which feeds a source solution, PH-adjusted liquid feeding system 305, mixing unit 306 which mixes the source solution, the PH-adjusted liquid and the sterilized water to prepare a nutrient solution suitable for culturing, and a nutrient solution feeding system 307 which feeds the mixed solution to the respective culturing units 100.

Figure 8:
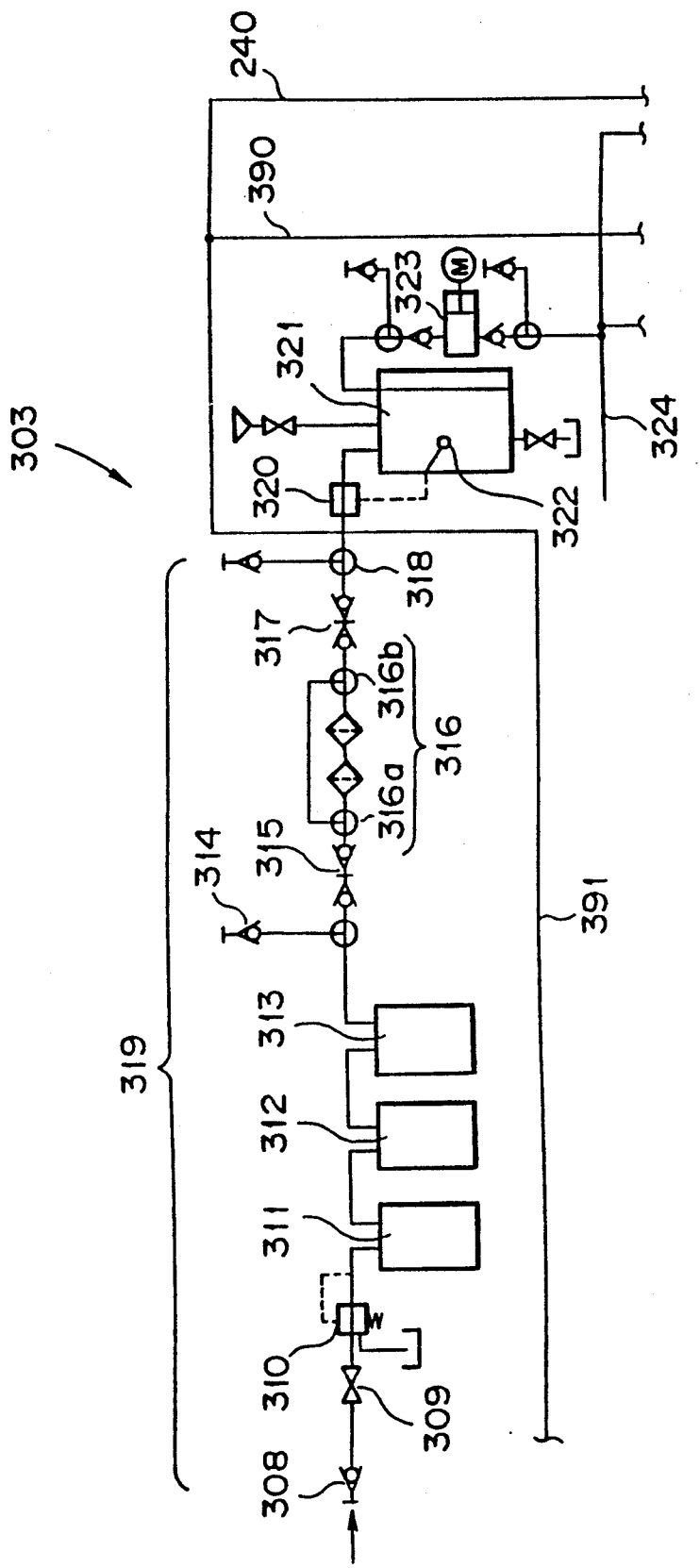
FIG. 8 illustrates a sterilized water feeding system.

As shown in FIG. 8, sterilized water feeding system 303 includes sterilizing unit 319 which comprises check-valved joint 308 connected to a water conduit (not shown), valve 309, relief valve 310, filter 311 using active carbon, first and second ion exchange resin units 312, 313, three-way joint 314, check-valved joint 315, filter 316 with three-way joint 316a at either end thereof and bypassable when the filter is exchanged, check-valved joint 317, and three-way joint 318. The water sterilized by sterilizing unit 319 is fed through valve 320 to and stored by sterilized water feeding reservoir tank 321. The water is also fed directly to first, second and third washing water feeding lines 240, 390 and 336. Reference numeral 322 denotes a float which opens valve 320 when a quantity of water in the sterilized water feeding tank decreases. Reference numeral 323 denotes first pump unit which pumps out pure water from sterilized water feeding tank 321. The first pump unit is connected to solution feeding system 304, mixing unit 306, third bus line 324 and second washing water feeding line 390.

Instead of sterilized water feeding line 319, a pure water reservoir tank may be connected to the distilled water pipe through a germ entrance-preventive joint. However, some immoderation can occur because of use of a large quantity of water.

Figure 9:
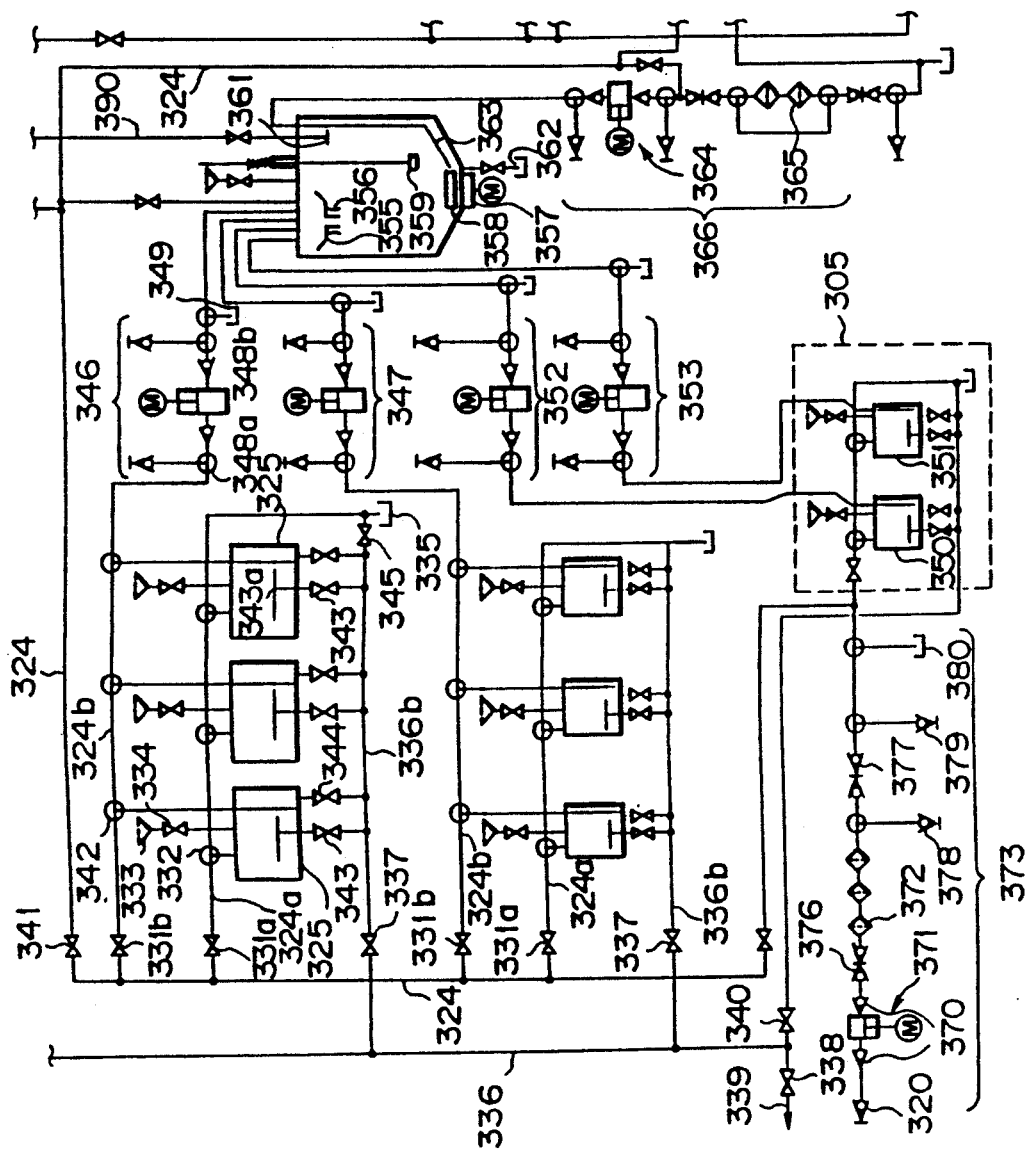
FIG. 9 illustrates a solution feeding system and a mixing unit.

As shown in FIG. 9, solution feeding system 304 includes first sterilizing line 373 which comprises second pump unit 371 which has check-valved joint 370 connectable to the source solution reservoir tank (not shown), and filter unit 372 disposed in order. The source liquid fed from the source liquid reservoir tank is sterilized by the first sterilizing line 373 and fed through third bus line 324 to first-sixth solution revervior tanks 325. The first sterilizing line 373 also includes check-valved joints 376, 377, three-way joints 378, 379 and drain 380 to perform sterilization when filter unit 372 is replaced.

The third bus line 324 branches through valves 331a, 331b to first and second branch lines 324a, 324b and leads at the other end through valve 341 to sterilized water feeding tank 321.

Third washing water feeding line 336 branching from sterilized water feeding line 319 (see FIG. 8) branches through valve 337 to third branch line 336b and also branches through valve 338 to sterilized water extracting port 339 which leads through valve 340 to PH-adjusted liquid feeding system 305.

Each solution feeding tank 325 is connected to first branch line 324a through three-way joint 332 and to second branch line 324b through three-way joint 342.

Further, each solution feeding tank 325 is connected to third branch line 336b through shower valve 343 and discharge valve 344, so that tank-washing pure water is fed to shower nozzle 343a through shower valve 343. Third branch line 336b is connected to drain 335 through valve 345.

The source liquid fed through third bus line 324 is fed through first branch line 324a to liquid feeding tank 325 by opening either one of valve 331a and solution tank 325, for example, three-way joint 332 of third solution tank 325. Reference numeral 333 denotes a breeder, and 334, a valve.

Thus, different solutions are fed into the corresponding solution feeding tanks. When feeding a solution into one solution feeding tank ends, sterilized water is fed from sterilizing water feeding line 319 to third bus line 324 by opening valve 344 and then from feeding valve 331a to drain 335 to thereby wash first branch line 324a.

Feeding solution from these solution feeding tanks 325 to mixing unit 306 is performed from second branch line 324b through third pump unit 346 by opening three-way joints 342 provided above the corresponding solution feeding tanks 325.

Third pump unit 346 has drain 349 and three-way joints 348a and 348b each of which is provided at corresponding end thereof through which sterilization is performed.

In this way, solution is fed through third pump unit 346 to the mixing unit. Emptied tank 325 is washed by feeding washing water from third branch line 336b to shower nozzle 343a through shower valve 343. At this time, valve 345 is closed. After washing, valves 344 and 345 are opened to discharge washing liquid to drain 335.

The solution feeding tanks are arranged in two series each including three tanks, and fourth pump unit 347 quite similar to third pump unit is disposed.

The two series of tanks are such that the tanks of one series have a larger capacity to accommodate a larger amount of solution used while the tanks of the other series has a smaller capacity to accommodate a smaller amount of solution used.

PH-adjusted liquid feeding system 305 also includes alkali feeding tank 350 and acid feeding tank 351 each of which has a structure similar to solution feeding tank 325. The tank interiors and connection lines are washed like solution feeding tank 325.

Alkali feeding tank 350 and acid feeding tank 351 are connected through fifth and sixth pump units 352 and 353, respectively, to the mixing unit. The fifth and sixth pump units are the same in structure as third and fourth pump units 346 and 347.

Mixing unit 306 includes mixing tank 354, diluting dish 355 and throttle 356 disposed in the upper portion of the mixing tank, stirrer 358 rotated externally by magnet 357, PH sensor 359, shower nozzle 361 which washes the tank inside and which is connected to sterilized water feeding line 319 through valve 360, and drain 362. A nutrient solution which is mixed so as to have desired components is fed to nutrient solution feeding system 307 through suction pipe 363 extending from the vicinity of the bottom of the mixing tank to seventh pump unit 364.

If the source liquid is directly entered into the tank, precipitation can occur, so that it is diluted with pure water in diluting dish 355 and then entered.

Reference numeral 365 denotes a filter unit which cooperates with seventh pump unit 364 to compose second sterilizing line 366 which has the same structure as first sterilizing line 373 which is used when the source liquid from the source liquid tank (not shown) is received.

In this way, as shown in FIG. 7, a nutrient solution is filled from mixing unit 306 through first nutrient solution line 382a into first-third nutrient solution tanks 381 of nutrient solution feeding system 307.

Nutrient solution feeding system 307 feeds a nutrient solution to culture box 106 through second nutrient solution feeding line 382b which comprises first to third nutrient solution feeding tanks 381 having exactly the same structure as the nutrient solution feeding tank, as mentioned above, and second nutrient solution feeding line 382b which feeds nutrient solution from first-third nutrient solution feeding tanks, and second bus line 301 which includes third sterilizing line 383. Third sterilizing line 308 includes pump unit 384 and filter unit 385 like the first and second sterilizing lines and is connected to second bus line 302 through valve 386.

Second bus line 301 includes, at an end, valve 387 and check-valved joint 388, and drain 389 and is connected at the other end to third sterilizing line 383 and also through valve 391 to first washing water feeding line 240 leading from sterilized water feeding unit 303. Second bus line 301 composes second bus line washing unit 302 which is capable of washing with sterilized water.

The discharge of nutrient solution from culture box 106 is performed by nutrient solution discharging line 395 which leads through valve 396 to breeder 397. Reference numeral 398 denotes a drain. Nutrient solution discharging line 395 is connected at the other end through valve 399 to first washing water feeding line 240.

Third bus line 324 is connected to second nutrient solution feeding line 382b through valve 393, so that predetermined solution may be added directly from the solution feeding tank (see FIG. 17).

According to such apparatus, the culture box is removable through the germ entrance-preventing joint, so that the culture box is easily sterilized. In addition, after the cultured tissues are bedded, the box is connected to the gas feeding unit and the solution feeding unit while keeping sterile conditions, so that contamination from mold or bacteria is greatly prevented.

The nutrient solution tanks are connected switchably from the common line to the culture box while the common line is washed with washing water including sterilized water each time the nutrient solution is changed. Therefore, the number of pump units required is reduced. Since in such apparatus "prevention of germ entrance" is considered most significant and germ entrance-preventive facilities are increased in scale in proportion to the number of pumps used, reduction of the number of pump units used is especially effective. While in the embodiment two series of tanks having different capacities are used, so that the two pump units are required, only one pump unit may be used if all the tank have the same capacity.

This applies to the pump units used for feeding solutions from the solution feeding tanks to the mixing unit.

Since in the apparatus various kinds of component solutions can be easily prepared in the mixing unit using different solutions from the solution feeding tanks, the solution components may be adjusted finely in accordance with the stage of growth of the cultured tissues to thereby expedite the growth and acclimation of the cultured tissues.

All parts such as filters required to be exchanged in use are connected through check-valved joints and effective for prevention of germ entrance in exchange.

While in the embodiment vermiculite is used as the nutrient medium support, polyester wool, peat moss or the like stable against ionization may be used. As for a nutrient medium support from which ions are eluted into the liquid in the sterilizing process or in the culture process, necessary measurement may be made for ions beforehand in which case the density of the ions in the nutrient solution can be adjusted and maintained under appropriate conditions.

Figure 10:
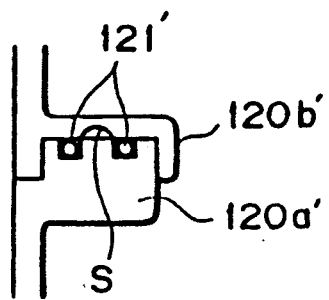
FIG. 10 illustrates a modification of a sealed structure of the culture box.

The hermetical sealing for the culture box is not limited to the structure shown in FIG. 3. As shown in FIG. 10, it may have a structure in which two O-like rings 121' are provided between body flange 120a' and lid flange 120b' and in which a gap S is eliminated.

Figure 11:
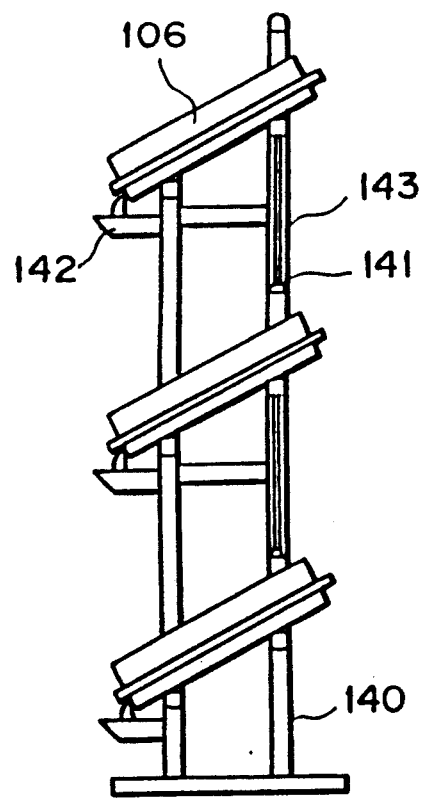
FIG. 11 illustrates the disposition of the culture box using the sun light.

Light source for illumination 129 is not limited to the metal halide lamp and sun light may be used instead. In this case, as shown in FIG. 11, culture boxes 106 may be attached at an angle to two supports 140 in order to improve the effeciency of using light and to effectively use the installation space. Reference numeral 141 denotes cooling water nozzles; 142, a cooling water basin; and 143, a cooling water pipe for facilitating the flow of cooling water.

Figure 12C:
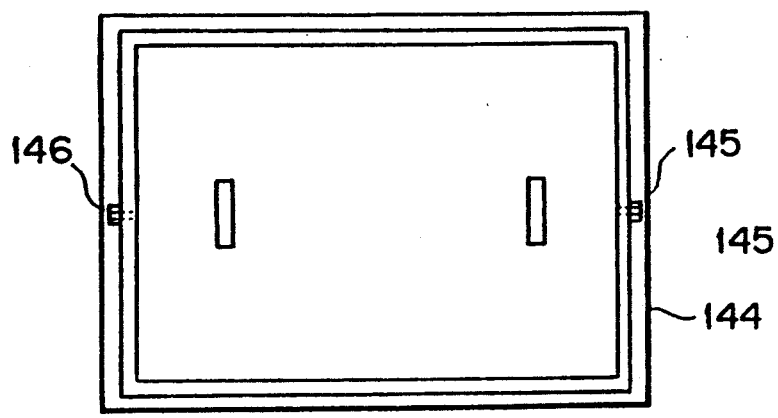
Figure 12C:
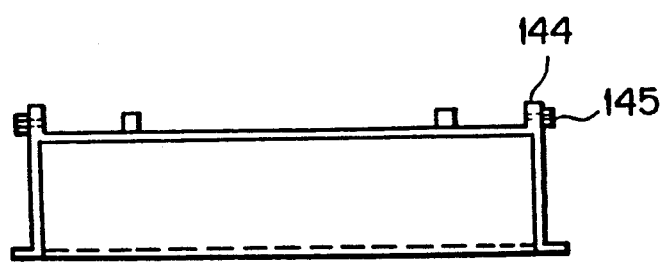

As shown in FIGS. 12(a), (b) and (c), frame 144 may be formed on culture box 106 such that cooling water is entered into the frame via cooling water feeding port 145 and discharged out of cooling water discharge port 146.

As shown in FIGS. 13(a), (b) and (c), the top and side of the culture box may be covered with frame 147 such that cooling water is supplied from cooling water feeding port 148 to cooling water discharge port 149.

Figure 14:
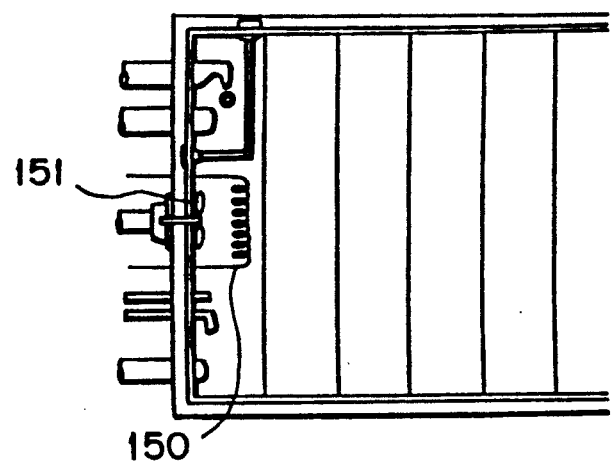
FIGS. 14.

As shown in FIG. 14, heat exchanger 150 may be provided within culture box 106 to cause fan 151 to stir air for temperature control. The fan may be used for forming a flow of wind within the box and young plants may be put under the stress of wind in the acclimating stage. Healthy plants strong against stress may be grown by such arrangement.

Prevention of germ entrance is further improved by replacing the fan with a magnetic stirrer.

The top of the culture box may have a roof-like shape to expedite the drop of droplets on the box inside. Alternatively, a magnetic wiper may be used to eliminate droplets.

Figure 15A:
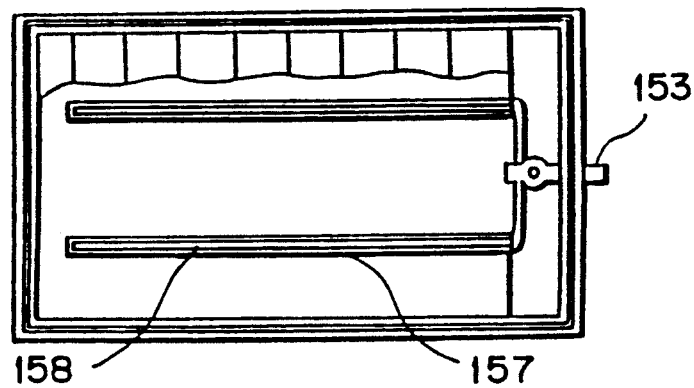
FIGS. 15(a) and (b) show modifications of the culture box.
Figure 15B:
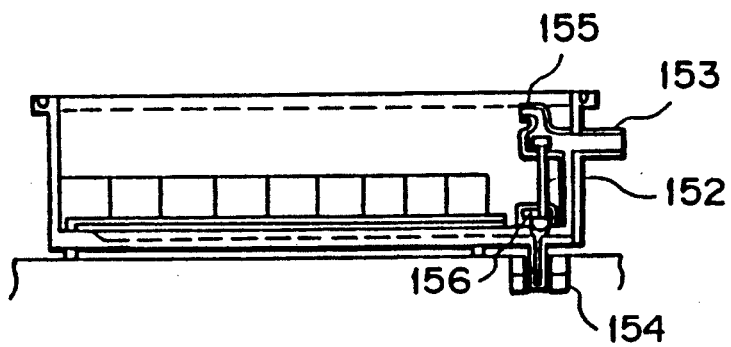
Figure 16:
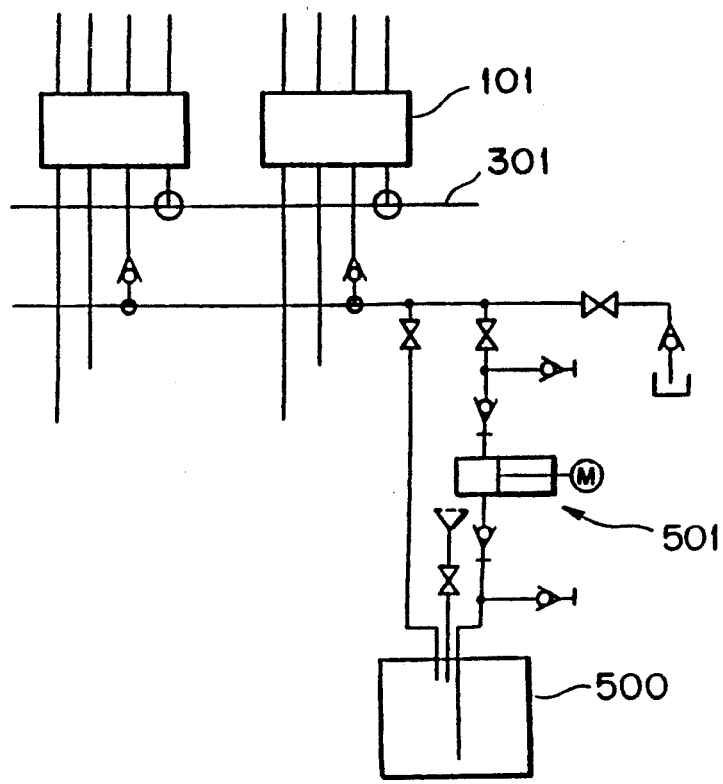
FIG. 16 illustrates a modification of a nutrient solution feeding system.

In addition, FIGS. 15(a) and (b) show a discharge pipe 153 with a changeover valve 152 instead of the gas discharge pipe and the nutrient solution discharge pipe of the culture box. Energization of magnet coil 154 operates changeover valve 152. When the changeover valve is moved upwardly, discharge nozzle 155 is closed while discharge nozzle 156 is opened and nutrient solution is discharged from discharge pipe 153. Conversely, if the changeover valve is lowered, gas is discharged. Instead of the capillary in the flange, groove 157 may be provided in the bottom of the culture box to accommodate capillary 158 therein in a compressed manner.

While in the embodiment exhaust liquid is shown as being discharged from the drain, it may be stored in discharge tank 500 and returned to the culture unit, as shown in FIG., 16. In this way, the liquid level may be moved upwardly or downwardly in accordance with the degree of growth of the young plants. Alternatively, a suction unit may be provided in the pipe to suction waste materials for recycling. Reference numeral 501 denotes a pump unit.

A second embodiment of the present invention will not be described in detail with reference to the drawings.

Figure 18:
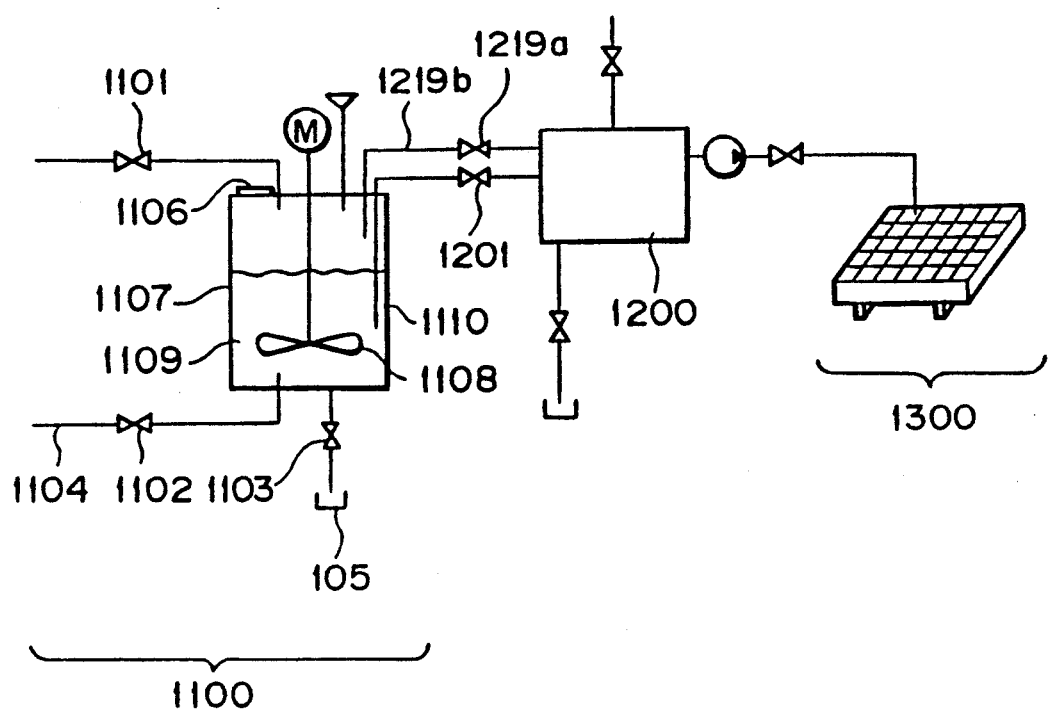
FIG. 18 schematically illustrates a bedding device as an embodiment of the present invention.

FIG. 18 illustrates the entire structure of the bedding apparatus of the inventive embodiment.

This bedding apparatus is used to bed the adventive embryos of carrots. It includes a culture unit 1100 which cultures calluses with a nutrient solution to form adventive embryos, selective unit 1200 which extracts a predetermined quantity of nutrient solution containing adventive embryos from culture unit 1100 and selecting the adventive embryos, and seedling unit 1300 which beds one of the adventive embryos, selected by the selective unit 1200, in each of unit areas of the culture box to thereby perform from callusing to bedding operations automatically.

Culture unit 1100 is connected through valve 1101 to the nutrient solution feeding system (not shown), to first discharge line 1104 and drain 1105 through valves 1102 and 1103, respectively. It also includes culture tank 1107 with germless cap 1106 for reception of calluses. Screw 1108 stirs nutrient solution 1109 containing callses entered into tank 1107 while maintaining a sterile state and expediting culture, and feeds an adventive embryo liquid formed by the culture to selective unit 1200 through suction pipe 1110.

Figure 19:
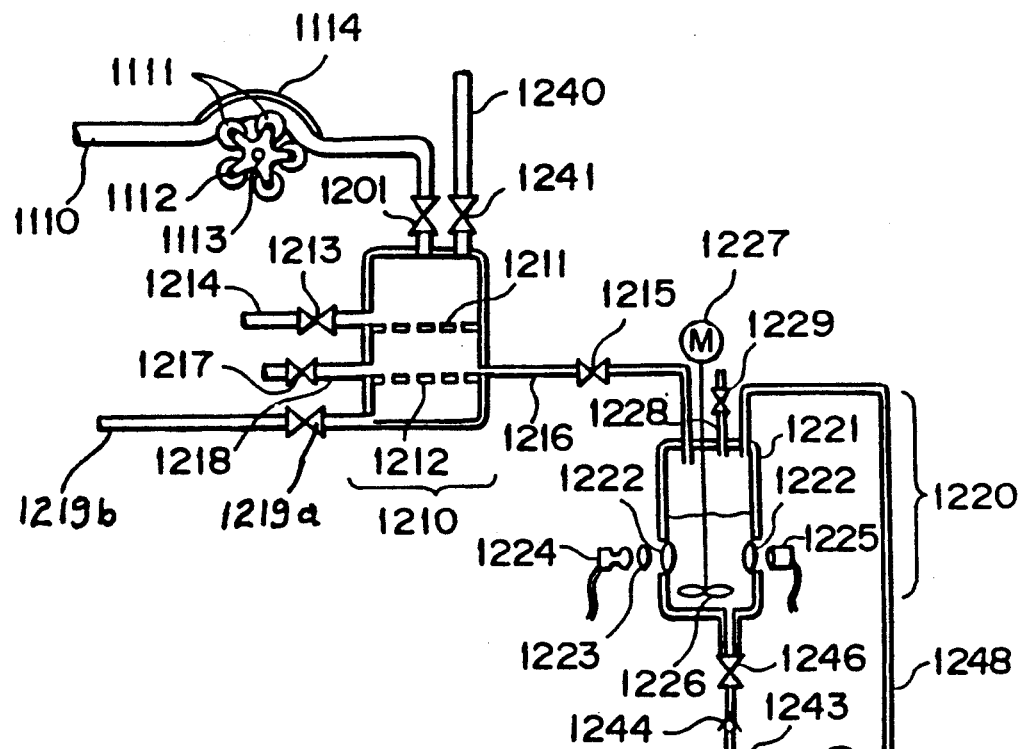
FIG. 19 illustrates a selecting unit of the bedding apparatus on enlarged scale.

As shown in FIG. 19, suction pipe 1110 is pressed at predetermined time intervals between guide 1114 and five rollers 1111 attached rotatably to hinge 1113 which rotates around pin 1112 to suck constant quantities of adventive embryo from culture tank 1107, due to a change in the suction pipe.

As shown in FIG. 19, selective unit 1200 selects good adventive embryos to be bedded from the adventive embryo nutrient solution led from suction pipe 1110 through valve 1201, and includes filter 1210, density adjuster 1220 and color determining unit 1230.

Filter 1210 includes first filter 1211 of a 100 $\mu$m-screen and a second filter 1212 of a 50 $\mu$m-screen. First filter 1211 filters out adventive embryos unsuitable for bedding due to being excessively large, discharge them through valve 1213 from second discharge line 1214, and feeds adventive embryos of an appropriate size (50 $\mu$m $<$ a $<$ 100 $\mu$m) remaining on the second filter, through valve 1215 from sending line 1216. Third discharge line 1218 connected through valve 1217 is used to return as an excess usable adventive embryos without feeding them to density adjusting unit 1220 when the density in the density adjusting unit 1220 is excessive. The culture liquid containing smaller adventive embryos which have passed through second filter is fed to first circulating line 1219b through valve 1219a and returned to culture tank 1107. Reference numeral 1240 denotes first adjusting pipe which feeds adjusting pure water or culture liquid when the density of adventive embryos in the culture liquid is excessively high and reference numeral 1241 a valve.

The density adjusting unit includes a light-screening container 1221 having a pair of opposing light-transparent windows 1222, first light emitting element 1224 provided through focusing lens 1223 at one light-transparent window 1222, and first photodetector 1225 disposed at the other window 1222 to thereby detect the density of the adventive embryos from the quantity of light detected by first photodetector 1225. Reference numeral 1226 denotes a stirring screw which is driven by motor 1227. The density is detected while the screw is being stirred, and the culture liquid or pure water is fed from second adjusting pipe 1228 until a predetermined density is reached at which time valve 1229 is closed immediately to stop the feed of the culture liquid or water so as to maintain the density of the adventive embryos within the container at a constant value at all times.

The culture liquid containing the adventive embryos adjusted in density in this way is fed to color determining unit 1230 such that a predetermined quantity of culture liquid pumped out by constant capacity pump 1243 driven by motor 1242 contains a single adventive embryo. Reference numerals 1244 and 1245 denote a check valve and 1246 a valve.

Figure 20:
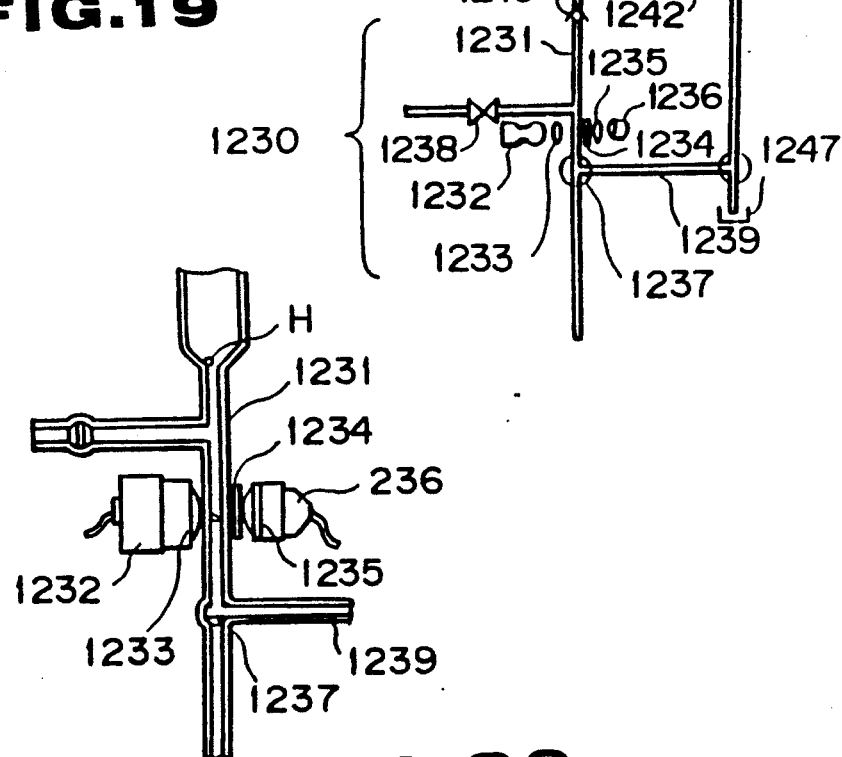
FIG. 20 illustrates a color determining unit of the selecting unit on enlarged scale.

Light is irradiated via a stop lens 1233 from second light emitting element 1232 onto culture liquid fed into detecting tube 1231, which is transparent to light, by a constant quantity by constant quantity pump 1243, as shown in FIG. 20 on enlarged scale. The light passing through the culture liquid is detected by second photodetector 1236 via color filter 1234 and stop lens 1235 to thereby detect the color and magnitude of the adventive embryos passing through detecting pipe 1231.

Reference numeral 1237 denotes a three-way valve which is operated so as to connect to bedding unit 1300 simultaneously with the detection of passage of adventive embryos H (FIG. 20) by second photodetector 1236 to open the pipe passage and valve 1238 so that the culture liquid is fed to bedding unit 1300 together with adventive embryos H.

A predetermined time later, valve 1238 is closed while three-way valve 1237 is opened to bypass pipe 1239. Thus, culture liquid is discharged through bypass pipe 1239 to drain 1247 or returned to the density adjusting unit through second circulating line 1248 until the second photodetector detects the passage of the next adventive embryo.

The adventive embryos are thus selected by the selective unit and fed one by one at predetermined intervals to bedding unit 1300.

Figure 21A:
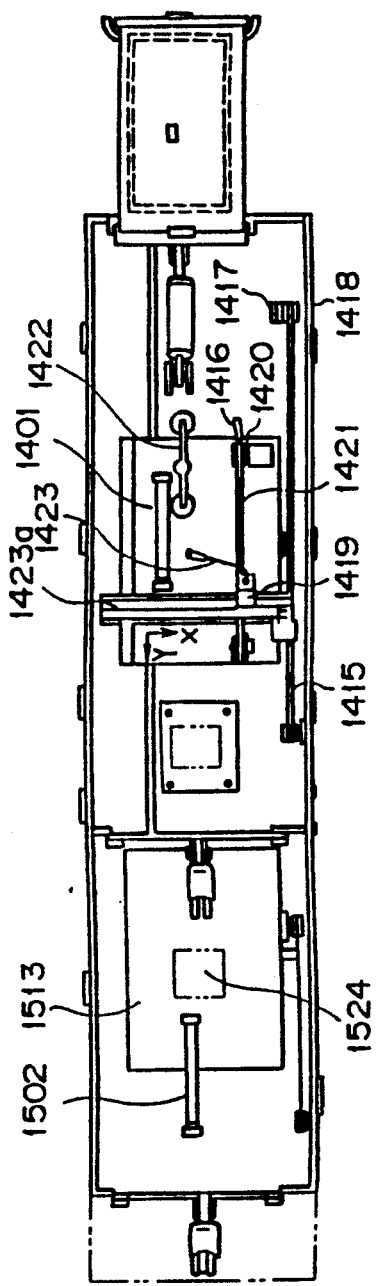
FIGS. 21(a) and (b) are a top plan view and a front view, respectively, of the bedding unit.
Figure 21B:
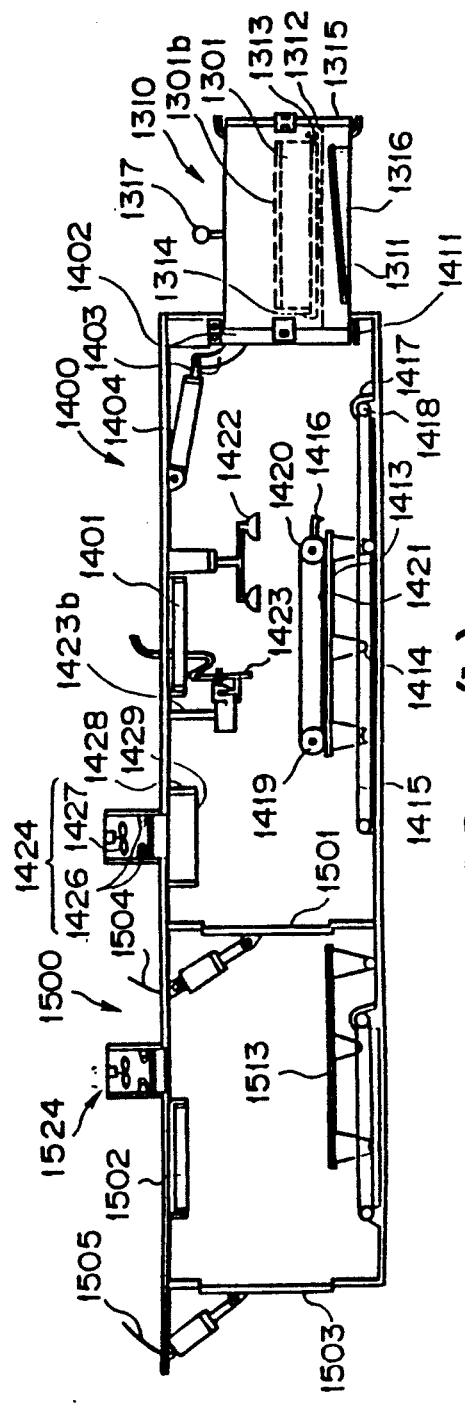

As shown in FIGS. 21(a) and in FIG. 21(b), bedding unit 1300 includes sterilizing chamber 1310 which sterilizes culture box 1301 in which adventive embryos are to be bedded, bedding chamber 1400 which beds in culture box 1301 adventive embryos fed from selective unit 1200 in culture box 1301, and post-chamber 1500 into which culture box 1301 after bedding is fed while maintaining the sterile state of the post-chamber. FIG. 21(a) is a top plan view of the bedding unit with an upper cover being removed away while FIG. 21(b) is a front view of the bedding unit with a side plate being removed away.

Sterilizing chamber 1310 has a hermetically sealed struture and contains water therein and has heater 1311 in the body of water so that steam is produced and the chamber is put at 121° C. and at 2 atms by the heat in order to sterilize culture box 1301 on transfer table 1313 put through a mesh-like base 1312. Transfer table 1313 has a hook 1314. Reference numeral 1315 denotes an inlet door for insertion of the culture box therethrough; 1316, a temperature sensor; and 1317, a pressure sensor.

Figure 22A:
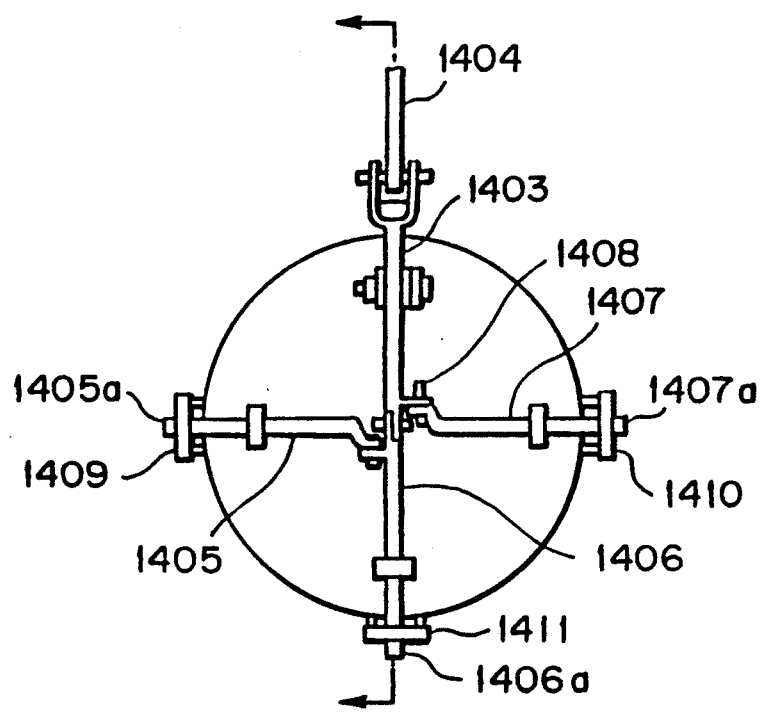
FIGS. 22(a) and (b) illustrate an inlet door for a bedding chamber of the bedding unit.
Figure 22B:
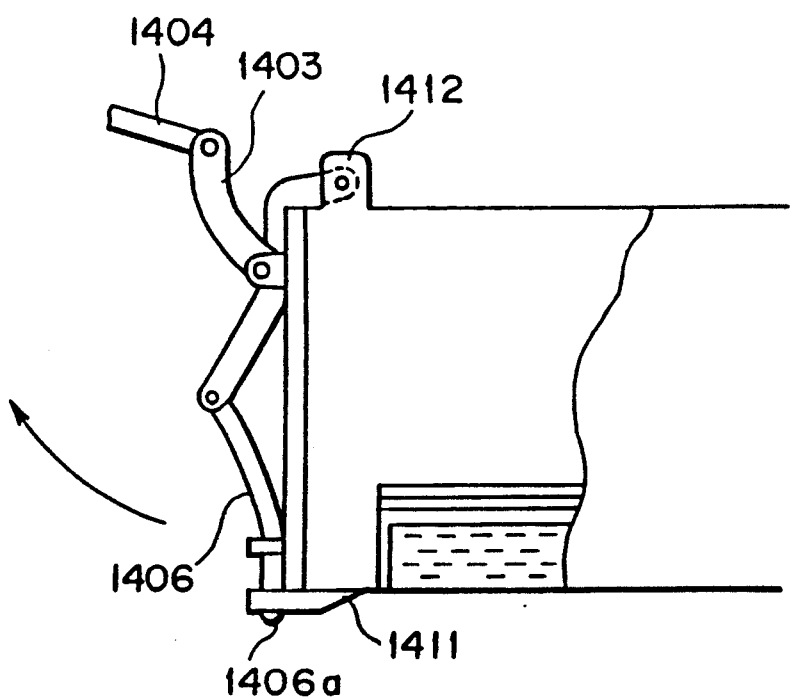

Bedding chamber 1400 maintains the chamber inside in a sterile state by sterilizing lamp 1401 which irradiates ultraviolet rays onto the chamber inside. As shown in FIGS. 22(a) and (b), when bracket 1403 is pushed rightward by cylinder 1404, bars 1405, 1406 and 1407 are drawn out through brackets 1408 and further through brackets 1409, 1410 and 1411 to thereby unhook hooks 1405a, 1406a and 1407a to open inlet door 1402, leading to sterilizing chamber 1310, with hinge 1412 as a fulcrum.

In this way, when the inlet door is opened, trunk 1413 is moved rightward by the movement of wire 1415 connected through clasp 1414, hook 1314 on transfer base 1313 is engaged with hook 1416, and culture box 1301 is dragged out together with the transfer base and entrained on truck 1413 and moved to a predetermined position. Wire 1415 is moved through pulley 1418 rotated by motor 1417. Similarly, hook 1416 is fixed to wire 1421 moving between pulleys 1419 and 1420 and moved.

Suction means 1422 is attached to the ceiling of the bedding chamber. Before bedding, lid 1301b of culture box 1301 is suctioned amd removed and, after bedding, the lid is again set.

Bedding nozzle 1423 is engaged with ceiling of the bedding chamber by bracket 1423b and beds adventive embryos, fed one by one at predetermined intervals from the selective unit, on the nutrient medium support. An end portion of bedding nozzle 1423 is movable in the X direction along guide 1423a while trunk 1413 is movable at predetermined pitches in the Y direction. After bedding, lid 1301b is returned to the predetermined position. Reference numeral 1424 denotes a filter device which includes filter 1425, ultraviolet lamp 1426 and heat radiating fin 1427. Plate 1429 is provided acting as a windshield on the lower surface of the filter device through bracket 1428.

Post-chamber 1500 is provided adjacent to bedding chamber 1400 through inlet door 1501 such that it is maintained in a sterile state by a sterilizing lamp comprising ultraviolet lamp 1502. The culture box is put together with transfer table 1313 by means of hook 1416 onto truck 1513 and moved. Reference numeral 1524 denotes a filter device identical in structure to filter device 1424.

Reference numeral 1503 denotes an outlet door. The inlet and outlet doors are opened when corresponding levers 1504 and 1505 are moved. It is arranged that the inlet and outlet doors are prevented from opening simultaneously by employing an interlock system. The culture box is taken out by opening the outlet door. It is arranged that after outlet door 1503 is once opened and then closed, inlet door 1501 is not opened until a predetermined time has passed to thereby complete sterilization of the inside of the post-chamber.

Figure 23:
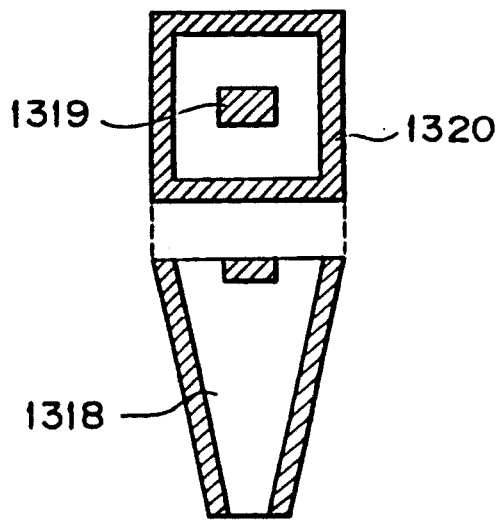
FIG. 23 illustrates a plug unit accommodated in the culture box.

As shown in FIGS. 23(a) and (b), culture box 1301 has a plurality of plug units arranged therein in columns and rows, each plug unit including bedding gel 1319 disposed within culture solution support 1318 of a material such as vermiculite or pearlite and surrounded by gel 1320. Each plug seedling unit may include several subunits.

In this way, adventive embryos alone are bedded very easily with high working efficiency under sterile conditions.

The adventive embryos may be grown in the post-chamber by feeding culture liquid and gas to the culture box.

Figure 24:
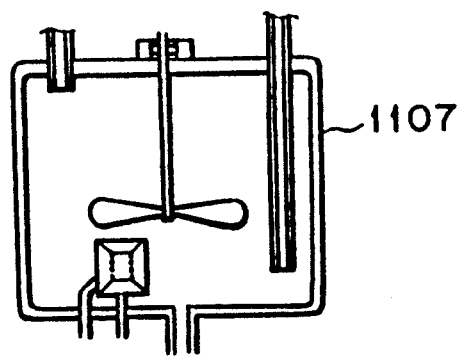
FIG. 24 illustrates a modification of a culture reservoir tank.

As shown in FIG. 24, if an axial flow filter is attached at the bottom of culture tank 1107, the tubular passageway of first discharge line 1104 is prevented from clogging.

In order to prevent clogging of first and second filters 1211 and 1212, they may be an axial flow type filter. Alternatively, either a flow generating circuit may be provided or mechanical vibrations may be imparted to the filters.

While the bedding nozzle is described as being movable in the X direction, it may arranged that a multiplicity of bedding nozzles are arranged in the X direction, and that adventive embryos fed from the selective unit are sequantially received and bedded together on in units of a row.

Figure 25:
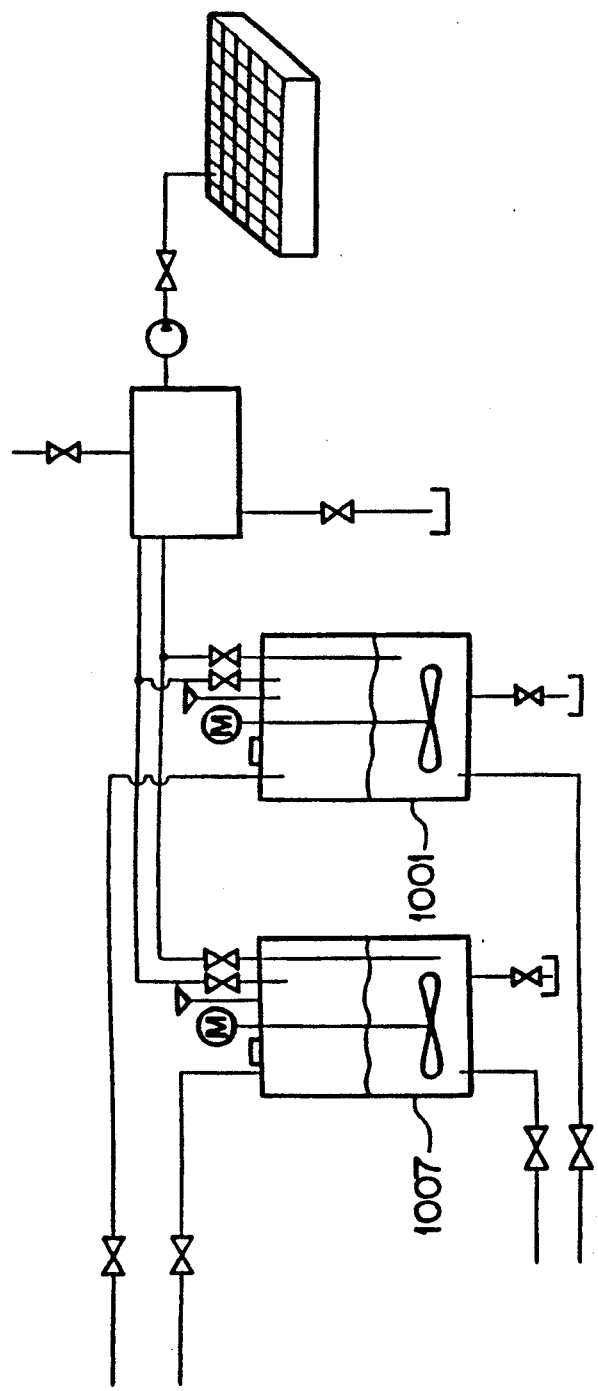
FIG. 25 illustrates another embodiment of the present invention.
Figure 26:
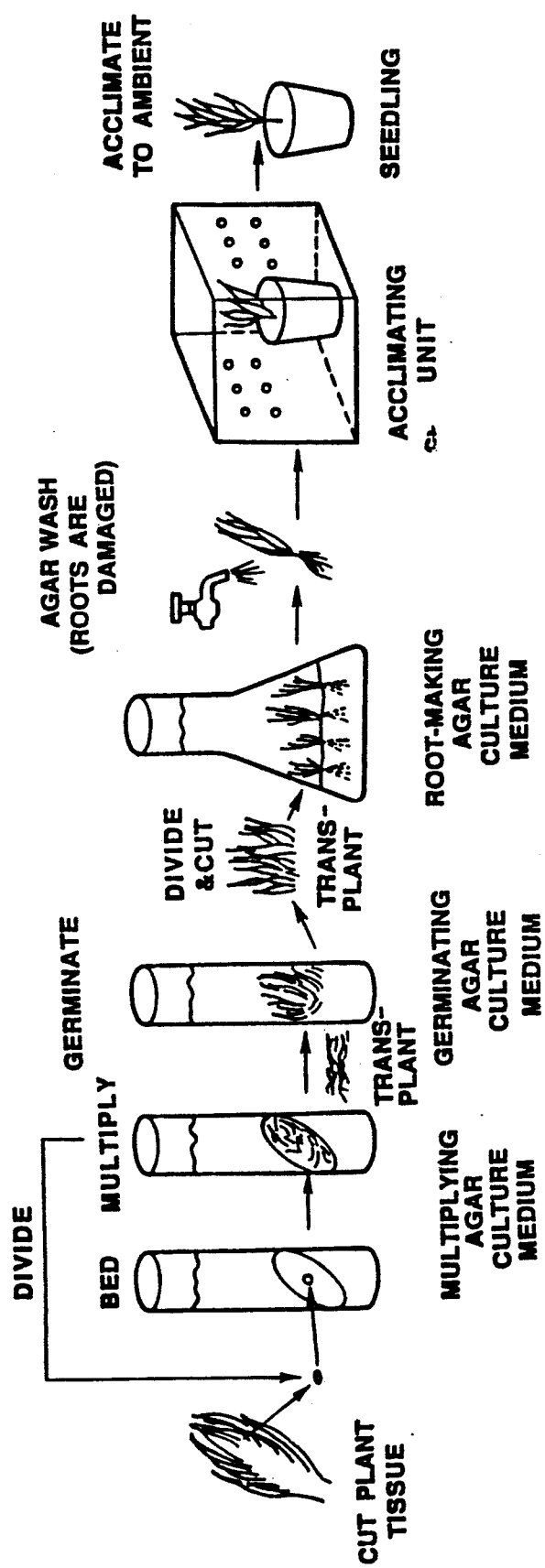
FIG. 26 is a conceptual illustration of a breeding method by shoot apex culturing.

While in the embodiment adventive embryos are described to be cultured in the culture tank, callus culturing tank 1007 may be added upstream of the culture tank which cultures adventive embryos, as shown in FIG. 25. This method permits the common use of the selective unit for selecting and culturing calluses to obtain good adventive embryos, so that the use of the apparatus is efficient. While selective unit 1200 uses three-way valve 1237, vibrations may imparted to the pipes concerned to ensure the selection of the adventive embryos and the movement of the adventive embryos in the culture liquid. Alternatively, electrodes may be provided within the pipes to draw adventive embryos or to move away adventive embryos from the pipes.

INDUSTRIAL APPLICABILITY

As described above, according to the present invention, a culture box having a nutrient medium support which is capable of holding a nutrient-solution nutrient medium is connected to a nutrient solution feeding system including a plurality of nutrient solution reservoir tanks and to a gas feeding system through removable germ entrance-preventive joints, so that a nutrient solution and a gas may be fed or discharged in a sterile state in accordance with the degree of growth of cultured tissues bedded on the nutrient solution nutrient medium to thereby achieve inexpensive and high speed growth of adventive embryos.

The inventive bedding apparatus includes culture means, means for selecting cultured tissues according to color and magnitude, and means for bedding the selected cultured tissue one by one on the nutrient medium at predetermined intervals. Therefore, selection and bedding are achieved very easily with high working efficiency under sterile conditions.

What is claimed is:

1. A bedding apparatus comprising:
   culture means for accommodating a cultured tissue together with a nutrient solution for culturing the tissue;
   means for selecting cultured tissues fed from the culture means according to color and magnitude of the cultured tissues;
   means for bedding the selected cultured tissues one by one on a nutrient medium at predetermined intervals;
   said selecting means including:
   means for detecting the density of the cultured tissues;
   means for feeding a nutrient solution or pure water to the cultures tissues until the density of the cultured tissues becomes a desired one in accordance with the output from the density detecting means;
   said selection means including:
   a detection pipe for passing therethrough a liquid adjusted in density by the density adjusting means such that a constant quantity of liquid contains a single cultured tissue; and
   tissue detecting means for detecting the magnitude of the cultured tissue from a quantity of light attenuation from the detecting pipe whereby the cultured tissues satisfying predetermined magnitude are fed to the bedding means.

2. A bedding apparatus according to claim 1, wherein the tissue detecting means further includes color filter means for checking whether the cultured tissue has a predetermined color or not.

3. A bedding apparatus comprising:
   culture means for accommodating a cultured tissue together with a nutrient solution for culturing the tissue;
   means for selecting cultured tissues fed from the culture means according to color and magnitude of the cultured tissues;
   means for bedding the selected cultured tissues one by one on a nutrient medium at predetermined intervals;
   the bedding means including a culture box;
   a chamber for sterilizing the culture box;
   a chamber for bedding sequentially cultured tissues guided from the selecting means into the culture box;
   a post-chamber including sterilizing means and taking out in a sterile state the culture box after the cultured tissues are bedded; and
   means for transferring the culture box sequentially through the respective chambers.

4. A bedding apparatus according to claim 3, wherein said chambers further include inlets and outlets, said chamber inlets and outlets are arranged so as not to open simultaneously, and wherein an interior of the bedding chamber is maintained at all times in a sterile state.

5. A bedding apparatus comprising:
   culture means for accommodating a cultured tissue together with a nutrient solution for culturing the tissue;
   means for selecting cultured tissues fed from the culture means according to color and magnitude of the cultured tissues; and
   means for bedding the selected cultured tissues one by one on a nutrient medium at predetermined intervals;
   said selecting means including:
   means for optically detecting the density of the cultured tissues; and
   means for feeding a nutrient solution or pure water to the cultured tissues until the density of the cultured tissues becomes a desired one in accordance with the output from the density detecting means.

6. A bedding apparatus according to claim 5, wherein said selecting means includes filter means which in turn includes a first filter and a second filter which is smaller in mesh than the first filter,
   wherein the first and second filters sequentially pass the cultured tissues therethrough such that possible substances remaining on the second filter are guided toward the bedding means.

* * * * *